United States Patent
Shuman

(10) Patent No.: US 10,799,221 B2
(45) Date of Patent: Oct. 13, 2020

(54) ELECTROMAGNETIC PIERCING DEVICES AND METHODS

(71) Applicant: Spiration, Inc., Redmond, WA (US)

(72) Inventor: Brandon J. Shuman, Kirkland, WA (US)

(73) Assignee: Gyrus ACMI, Inc., Southborough, MA (US)

( * ) Notice: Subject to any disclaimer, the term of this patent is extended or adjusted under 35 U.S.C. 154(b) by 129 days.

(21) Appl. No.: 16/084,888

(22) PCT Filed: Mar. 23, 2016

(86) PCT No.: PCT/US2016/023690
§ 371 (c)(1),
(2) Date: Sep. 13, 2018

(87) PCT Pub. No.: WO2017/164858
PCT Pub. Date: Sep. 28, 2017

(65) Prior Publication Data
US 2019/0076134 A1 Mar. 14, 2019

(51) Int. Cl.
*A61B 10/02* (2006.01)
*A61B 10/06* (2006.01)

(52) U.S. Cl.
CPC ...... *A61B 10/0266* (2013.01); *A61B 10/0283* (2013.01); *A61B 10/06* (2013.01); *A61B 2010/0208* (2013.01); *A61B 2010/0225* (2013.01)

(58) Field of Classification Search
CPC . A61B 10/0266; A61B 10/0283; A61B 10/06; A61B 2010/0208; A61B 2010/0225; A61B 10/02
See application file for complete search history.

(56) References Cited

U.S. PATENT DOCUMENTS

| 5,916,229 | A | 6/1999 | Evans |
| 6,702,761 | B1 | 3/2004 | Damadian |
| 2013/0006225 | A1 | 1/2013 | Cucin |
| 2013/0030323 | A1 | 1/2013 | Smith |
| 2014/0257438 | A1* | 9/2014 | Simon ............... A61N 2/008 607/72 |

* cited by examiner

*Primary Examiner* — George J Ulsh

(57) ABSTRACT

A device for providing a magnetic force to a sampling needle. The device may include with a sheath having a proximal end and a distal end, a needle slidably received within the distal end of the sheath and an actuator component located at least partially within the distal end of the sheath, the actuator component configured to apply a magnetic force to the needle. The actuator component may include a coil located within the distal end of the sheath and a current source in electrical communication with the coil. The current source may include one or more capacitors, a DC power source, a first switch configured to cause the DC power source to charge the capacitors upon activation and a second switch configured to cause the capacitors to discharge to the coil upon activation.

6 Claims, 6 Drawing Sheets

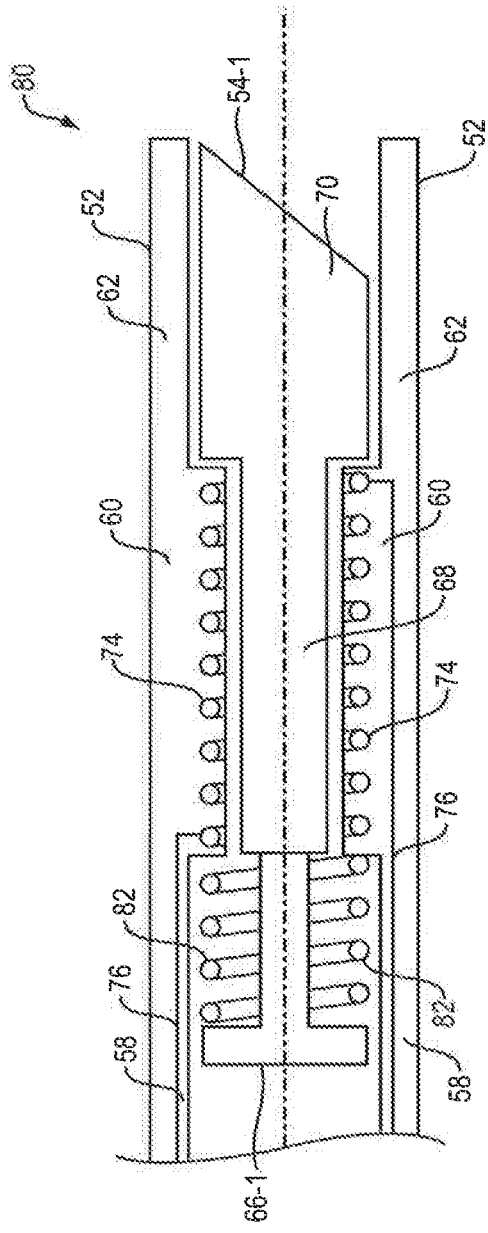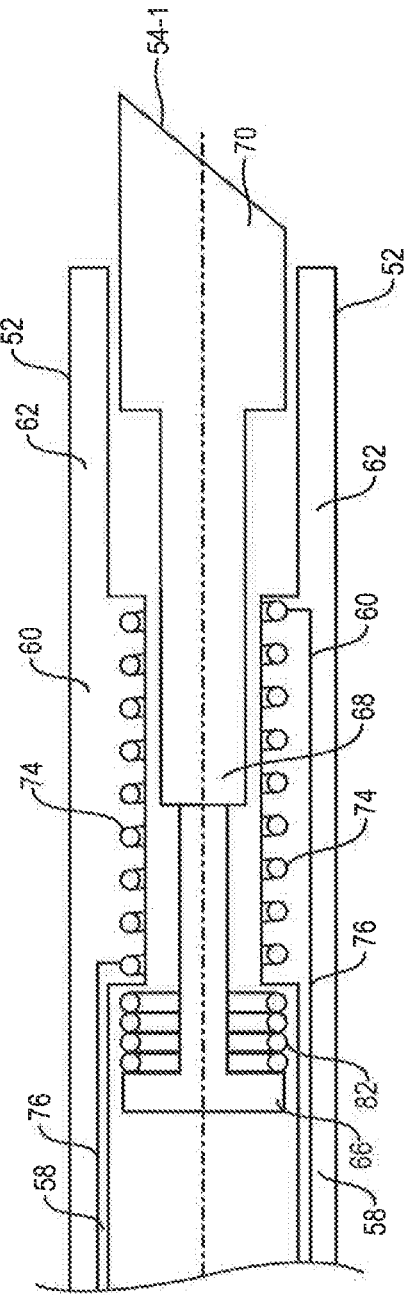

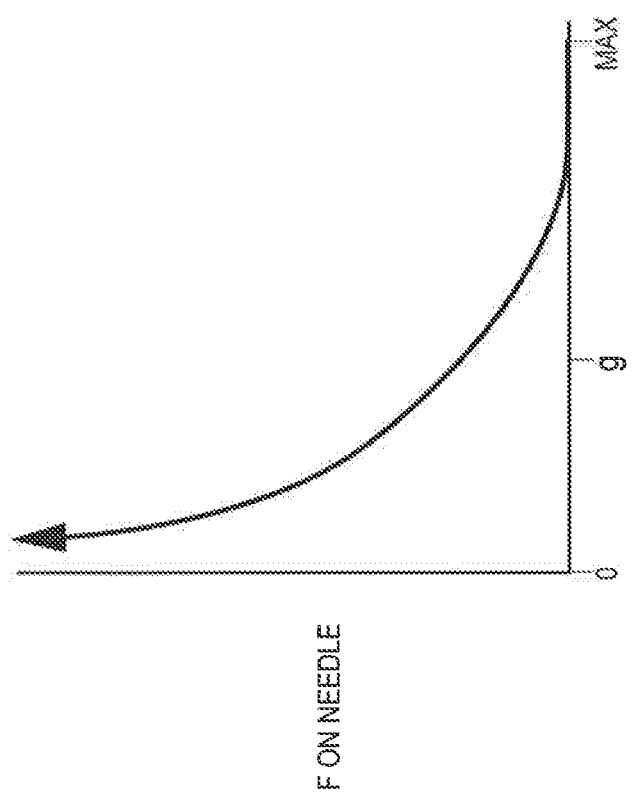

ELECTROMAGNETIC PIERCING DEVICES AND METHODS

FIELD

The present teachings relate to medical devices, and more particularly, to improved methods and devices for sampling a target tissue.

BACKGROUND

Piercing a needle into tissue sometimes requires a significant amount of force applied to the needle. Transmitting that force to a needle within a long catheter lumen can cause mechanical challenges, such as unwanted friction or inconsistent force application.

SUMMARY

The present teachings provides a tissue piercing system. The present teachings provide a device with a sheath having a proximal end and a distal end, a needle slidably received within the distal end of the sheath and an actuator component located at least partially within the distal end of the sheath, the actuator component configured to apply a magnetic force to the needle. The actuator component may include a coil located within the distal end of the sheath and a current source in electrical communication with the coil.

The present teachings further provide that the current source includes one or more capacitors, a DC power source, a first switch configured to cause the DC power source to charge the capacitors upon activation and a second switch configured to cause the capacitors to discharge to the coil upon activation.

BRIEF DESCRIPTION OF THE DRAWINGS

FIGS. 4-1 and 4-2 illustrate cross sectional views of a piercing device during different operational modes according to the teachings herein;

FIGS. 5-1 and 5-2 illustrate cross sectional views of another piercing device during different operational modes according to the teachings herein;

FIG. 6 illustrates a force curve associated with the piercing device shown FIGS. 4-1 and 4-2.

DETAILED DESCRIPTION

Figure 1:
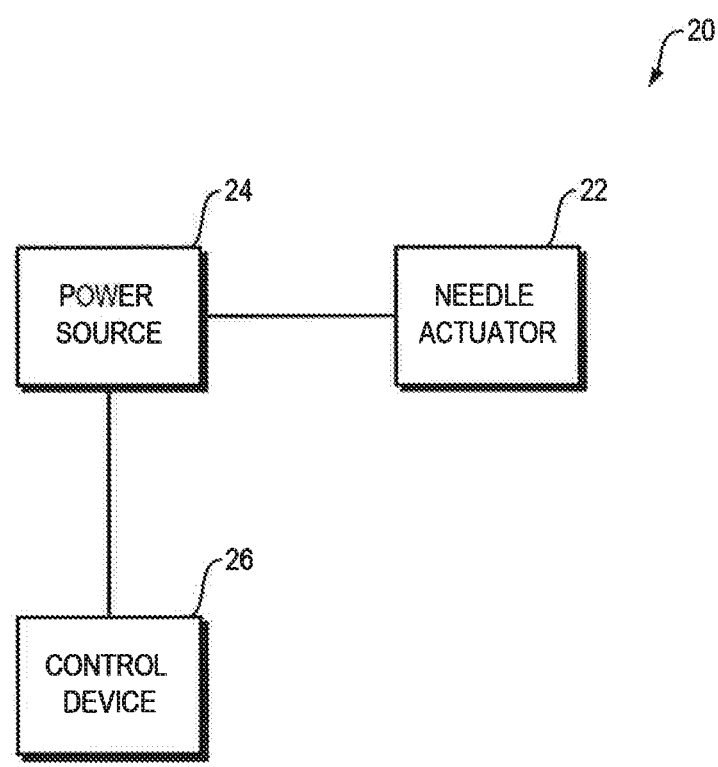
FIG. 1 illustrates a block diagram of a components of a piercing system according to the teachings herein.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the description herein, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

While the teachings herein refer to and reference terms like "bronchoscope", "catheter", "nodule", "device", "needle", "sampling needle" and the like, it is understood that these terms are broad, and the teachings herein can be used without limitation. In other words, the teachings herein may be suitable for sampling other vessels, passages, lumens, body cavities, anatomy, tissue, organs, the like, or a combination thereof in humans and animals. One or more devices may function to pierce a target tissue, thus improving needle sampling operation. The one or more devices may be included in a bronchoscope.

One or more bronchoscopes may be or may provide a device for attaching to a piercing device that can repeatedly pierce a target tissue. The one or more bronchoscopes may provide for insertion, manipulation, and operation of various surgical instruments in the anatomy of a patient. The one or more bronchoscopes may provide for delivery of one or more piercing devices into the anatomy. The one or more bronchoscopes may be used to visually inspect a site of interest, like the airways and lungs of a patient. The one or more bronchoscopes may be used to examine, treat, and/or diagnose lung growth, lung problems, lung cancer, lymph node(s), atelectasis, suspected interstitial lung disease, a lung rejection after a lung transplant, and/or to remove fluid or mucus plugs from the airways of a patient. The one or more bronchoscopes may be at least partially flexible, at least partially rigid, or both. The one or more bronchoscopes may include one or more ultrasound probes.

One or more catheters may function to provide a channel, a lumen, an opening, and/or a passageway for one or more sampling devices to be advanced and/or introduced into the anatomy. The one or more catheters may function to introduce into the anatomy one or more medical devices, needles, transbronchial needle aspiration devices, cytology brushes, biopsy forceps, guiding devices, ultrasonic probes, illumination, devices, therapies (i.e., chemotherapy, proteinomics, microspheres, etc.), the like, or a combination thereof. The one or more catheters may be used to remove or expel from the anatomy one or more devices, fluids, tissue samples, abnormalities, foreign matter, or a combination thereof. The one or more catheters may each contain one or more lumen. The one or more catheters may include one or more sections that are generally rigid, one or more sections that are generally flexible, or a combination of both. The one or more catheters may include one or more sections that are generally rigid, generally flexible, or a combination of both. The one or more catheters may be at least partially flexible, bendable, articulable, or a combination thereof so that access to regions of interest can be easily obtained. The one or more catheters may bend or articulate 15 degrees or more, 45 degrees or more, 60 degrees or more, 90 degrees or more, 110 degrees or more, or even 130 degrees or more. The one or more catheters may be fabricated from a polymer, nylon, silicon, or any other suitable material. An outer surface of the one or more catheters may include a lubricant to facilitate insertion into, and removal from, the anatomy, the bronchoscope, a working channel of the bronchoscope, or a combination thereof. The one or more catheters may be elongated tubular members. The one or more catheters may extend along a longitudinal axis, a catheter axis, or both. The one or more catheters may include a uniform cross section, or the cross section may vary, taper, widen, narrow, or a combination thereof. The cross section of the one or more catheters may be circular, oval, irregular, and/or any other suitable shape or configuration. The cross section of the one or more catheters may be expandable, collapsible, formable, deformable, or a combination thereof. The one or more catheters may be configured to house, contain and/or protect any size or gauge needle. For example, the one or more catheters may house, contain, and/or protect about a 25 gauge needle or more, about a 22 gauge needle, about a 21 gauge needle, about a 19 gauge needle or less, etc. An outer surface of the one or more catheters may include one or more echogenic features or scribes. The one or more catheters may include one or more echogenic features so that the position and orientation of the catheter, the device, the needle, the needle tip, or a combination thereof can be viewed. The one or more catheters may include or define a hole or opening at a distal end, a proximal end, at a region in between, or a combination thereof so that one or more devices or instruments can pass therethrough. The one or more catheters may include or define an inner surface, an inner diameter, an inner portion, or a combination thereof that is dimensioned to generally conform to the outer diameter of the one or more sampling needles or sampling needle sheath.

One or more needles may function to be advanced into the anatomy to penetrate a site or region of interest. The one or more needles may function to repeatedly puncture a region of interest for tissue sampling. The one or more needles may also function to provide medicine, therapy, or both to the anatomy. The one or more needles may also function to provide, develop, or have a local vacuum to a distal end or at a distal tip thereof. The one or more needles may be advanced towards and retracted from the region of interest via an inductor coil. The one or more needles may be at least partially contained within a catheter. The one or more needles may be moved, advanced, retracted, or a combination thereof in the catheter. The one or more needles may have a length that extends along a longitudinal axis, a needle axis, or both. The one or more needles may have a constant cross section, a varying cross section, a tapered cross section, an irregular cross section, or a combination thereof. The cross section of the one or more needles may be generally circular, oval, irregular, or any other suitable shape. The one or more needles may be generally hollow. The one or more needles may include a generally concentric outer diameter and inner diameter. The one or more needles may have an outer diameter and an inner diameter, one or more of which may have a constant size along a length of the needle. The one or more needles may have an outer diameter and an inner diameter, one or more of which may vary, taper, slope, change, or a combination thereof. The one or more needles may be formed from a single material, or may be formed from one or more materials. The one or more needles may be fabricated from any material suitable for use in medical procedures. The one or more needles may be made from a metal or metal alloy, such as stainless steel, nitinol, or the like. The one or more needles may include a polymer or other suitable covering. The one or more needles may be generally rigid, generally flexible, or both. The one or more needles may include one or more portions or sections that are generally rigid, one or more portions or sections that are generally flexible, or both. The one or more needles may be at least partially flexible, bendable, articulable, or a combination thereof so that access to regions of interest can be easily obtained. The one or more needles may bend or articulate about 15 degrees or more, about 45 degrees or more, about 60 degrees or more, about 0 degrees or more, about 110 degrees or more, or even about 130 degrees or more. The one or more needles may be constructed from one or more hypotubes. The one or more needles may be constructed from one or more hypotubes that are relatively smooth and able to freely slide, rotate, or otherwise move within a sheath, a catheter, a bronchoscope, a device, the anatomy, or a combination thereof. The one or more needles may include one or more holes, ports, slots, apertures, openings, the like, or a combination thereof at the distal end, a proximal end, or a location therebetween. The one or more needles may include one or more holes, ports, slots, the like or a combination thereof for tissue sample collection; for introducing one or more stylets; for introducing medicine or therapy to the anatomy; or a combination thereof.

The one or more needles may be any size or gauge. That is, the one or more needles may be about 25 gauge or more, about 22 gauge, about 21 gauge, or about 19 gauge or less, etc. The one or more needles may include a combination of two or more gauges. That is, for example, a proximal portion of the needle may be about 21 gauge and a distal portion of the needle may be about 19 gauge, or vice versa. The one or more needles may include two or more needle portions that are joined together fixedly, permanently, temporarily, or a combination thereof. The two or more needle portions may be the same gauge, or may be different gauges. One or both of the needle portions may include an interior size or region that is generally the same size as the one or more stylets. That is, the one or more stylets may substantially occupy some, most, or all of the interior of the one or more needles, needle portions, or both. One or both of the needle portions, the needle, or both may be slightly larger than the one or more stylets, so that the stylets only occupy some of the interior space or region of the one or more needles, needle portions, or both. The one or more needles may include an elongated section, member, or shaft and a distal tip or needle tip. The elongated section, the needle tip, or both may include one or more, or even two or more echogenic markings or scribes. The one or more echogenic features may function to enhance the visibility of the catheter, the needle, the needle tip, or a combination thereof. The one or more echogenic features may function to create one or more echogenic reflections during ultrasonic imaging so that a position or location of the catheter, the needle, and/or the needle tip within the anatomy can be determined. The one or more echogenic features may be or may include one or more scribes, bands, slots, segments, shapes, surfaces, recesses, roughened surfaces, embedded material(s), coatings, grooves, serrations, notches, or a combination thereof. The one or more echogenic features may be one or more dimples, scallops, spiral scribes, helixes, squiggles, angled squiggles, jig-saws, symmetrical shapes, asymmetrical shapes, patterns, dots, dashes, lines, formations, or a combination thereof. The one or more needles may include a distal tip.

The distal end of the needle, the distal tip, the needle tip, or a combination thereof may be configured to function as a piercing tip or feature so that cells, tissue, foreign matter, or a combination thereof can be obtained. The needle tip may be angled, sharply angled, beveled, flat, or a combination thereof so that tissue samples can be cut, cored, scraped from a site or region of interest. The needle tip may include a notched portion, a recessed portion, and/or a lancet tip or feature. A local vacuum may be created or formed at a distal end of the needle, a distal portion, or a needle tip so that tissue samples, foreign matter, or both can be aspirated or moved into the needle, the sample storage area, or both. The one or more needle tips may be contained within the one or more catheters as the catheter is advanced through the anatomy towards the site or region of interest. The one or more needle tips may be advanced or extended past a distal end of the one or more catheters when the catheter is near the region of interest. The one or more needle tips may be generally rigid, flexible, or both. The distal end, the needle tip, or both may include one or more echogenic features. The one or more needles may include one or more sample storage areas.

One or more sheaths may function to be advanced into the anatomy. The one or more sheaths may also function to provide medicine, therapy, or both to the anatomy. The one or more sheaths may also function to provide, develop, or have a local vacuum to a distal end or at a distal tip thereof. The one or more sheaths may be advanced towards and retracted from the region of interest via a handle device. The one or more sheaths may be at least partially contained within a catheter. The one or more sheaths may be moved, advanced, retracted, or a combination thereof in the catheter. The one or more sheaths may have a length that extends along a longitudinal axis, a needle axis, or both. The one or more sheaths may have a constant cross section, a varying cross section, a tapered cross section, an irregular cross section, or a combination thereof. The cross section of the one or more sheaths may be generally circular, oval, irregular, or any other suitable shape. The one or more sheaths may be generally hollow. The one or more sheaths may include a generally concentric outer diameter and inner diameter. The one or more sheaths may have an outer diameter and an inner diameter, one or more of which may have a constant size along a length of the needle. The one or more sheaths may have an outer diameter and an inner diameter, one or more of which may vary, taper, slope, change, or a combination thereof. The one or more sheaths may be formed from a single material, or may be formed from one or more materials. The one or more sheaths may be fabricated from any material suitable for use in medical procedures. The one or more sheaths may be made from a plastic tubing, or the like. The one or more sheaths may be generally rigid, generally flexible, or both. The one or more sheaths may include one or more portions or sections that are generally rigid, one or more portions or sections that are generally flexible, or both. The one or more sheaths may be at least partially flexible, bendable, articulable, or a combination thereof so that access to regions of interest can be easily obtained. The one or more sheaths may bend or articulate about 15 degrees or more, about 45 degrees or more, about 60 degrees or more, about 0 degrees or more, about 110 degrees or more, or even about 130 degrees or more. The one or more sheaths may be constructed to be relatively smooth and able to freely slide, rotate, or otherwise move within a catheter, a bronchoscope, a device, the anatomy, or a combination thereof. The one or more sheaths may include one or more holes, ports, slots, apertures, openings, the like, or a combination thereof at the distal end, a proximal end, or a location therebetween. The one or more sheaths may include one or more holes, ports, slots, the like or a combination thereof for introducing a stylet, medicine or therapy to the anatomy or a combination thereof.

The one or more sheaths may be any size or gauge. That is, the one or more sheaths may be about 25 gauge or more, about 22 gauge, about 21 gauge, or about 19 gauge or less, etc. The one or more sheaths may include a combination of two or more gauges. That is, for example, a proximal portion of the sheath may be about 2.1 gauge and a distal portion of the sheath may be about 19 gauge, or vice versa. The one or more sheaths may include two or more sheath portions that are joined together fixedly, permanently, temporarily, or a combination thereof. The two or more sheath portions may be the same gauge, or may be different gauges. One or both of the sheath portions may include an interior size or region that is generally the same size as the needles or the one or more stylets. That is, the needles or the one or more stylets may substantially occupy some, most, or all of the interior of the one or more sheaths, sheath portions, or both. One or both of the sheath portions, the sheath, or both may be slightly larger than the needles or the one or more stylets, so that the stylets only occupy some of the interior space or region of the one or more sheaths, sheath portions, or both. The one or more sheaths may include an elongated section, member, or shaft. The elongated section may include one or more, or even two or more echogenic markings or scribes. The one or more echogenic features may function to enhance the visibility of the catheter, the sheath, or a combination thereof. The one or more echogenic features may function to create one or more echogenic reflections during ultrasonic imaging so that a position or location of the catheter, the sheath within the anatomy can be determined. The one or more echogenic features may be or may include one or more scribes, bands, slots, segments, shapes, surfaces, recesses, roughened surfaces, embedded material(s), coatings, grooves, serrations, notches, or a combination thereof. The one or more echogenic features may be one or more dimples, scallops, spiral scribes, helixes, squiggles, angled squiggles, jig-saws, symmetrical shapes, asymmetrical shapes, patterns, dots, dashes, lines, formations, or a combination thereof.

The one or more sheaths may include a needle housing area located at a distal end for receiving at least a portion of the needle. The needle housing area may include one or more needle advancing stops that engage with one or more flanges of the needle. The housing area may also include one or more needle retracting stops that engage with one or more other flanges of the needle. The one or more sheaths and/or a handle may include one or more electromagnetic actuators and a power source for driving one or more electromagnetic actuators. The electromagnetic actuators may include one or more coils embedded into the sheath or may be positioned along an inner wall of the sheath, or a combination thereof. The power source may electrically connect to the coils for providing a current thereto. The power source may be located at a handle for the sheath and/or the needle, at a bronchoscope handle, remote from either the handle or the bronchoscope, or a combination thereof.

One or, more stylets may be disposed within the sheath or the needle such that the distal ends of the stylet and the needle are substantially aligned. The one or more stylets may function to block or prevent debris (i.e., tissue, blood, and the like) from entering the needle as needle is advanced towards a site or region of interest. The one or more stylets may be formed from a single material, or may be formed from one or more materials. The one or more stylets may be fabricated from any suitable material. The one or more stylets may be made from a metal or metal alloy, such as stainless steel, nitinol, or the like. The one or more stylets may be formed from a shape memory material (i.e., metal or polymer). The one or more stylets may include a polymer or other suitable covering over at least a portion of the length of the stylets. The one or more stylets may be at least partially rigid at least partially flexible, or both. The one or more stylets may include one or more portions (i.e., a distal portion, a proximal portion, or a portion in between) that are at least partially rigid, at least partially flexible, or both. The one or more stylets may be at least partially flexible, bendable, articulable, or a combination thereof so that the stylet can be positioned along a central lumen, opening, and/or interior portion of the needles. The one or more stylets may bend or articulate about 15 degrees or more, about 45 degrees or more, about 60 degrees or more, about 90 degrees or more, about 110 degrees or more, or even about 130 degrees or more. The one or more stylets may have a generally uniform cross section, or the cross section may be variable. At least a portion of the outer surface of the one or more stylets may be substantially the same size as the interior of one or more needle portions of the one or more needles so that the stylet substantially occupies some, most, or all of the interior of the needle. The one or more stylets may be advanced, actuated, or moved from a retracted position to an advanced, position. In the retracted position, the distal end of the one or more stylets may be offset or retracted from the distal end of the one or more needles for receiving tissue samples. In the advanced position, the distal end of the one or more stylets may be substantially aligned with the distal end of the one or more needles to form a substantially continuous surface or edge. When the needle and stylet extend beyond a distal end of the catheter, the needle can penetrate and separate tissue without coring, ripping, or damaging the tissue. The one or more stylets may include one or more notched portions, recesses, cut-outs, or grooves. The one or more notched portions, recesses, cut-outs, or grooves may be located at a distal end or at a location between the distal and proximal ends of the stylet. The one or more stylets may be at least partially withdrawn from the one or more needles.

The sampling direction may be a direction where the needle is extended out from the sheath, into tissue. The sampling direction may be movement of the needle towards a site of interest, into a site of interest, or both. The sampling direction may be an opposite direction as a retention direction.

The retention direction may be a direction where a sample is removed from a site of interest. The retention direction may be in a direction opposite radial expansion of a retaining mechanism. The retention direction may be a direction that prevents a sample from being removed from a needle.

FIG. 1 illustrates components of a needle piercing system 20 that includes a needle actuator 22, a power source 24 and a control device 26. The needle piercing system 20 may be a magnetic pulse accelerator similar to that used in a coil gun. The control device 26 controls current output by the power source 24 and thus activation of the needle actuator 22. Activation of the needle actuator 22 applies a magnetic force to a sampling needle.

Figure 2:
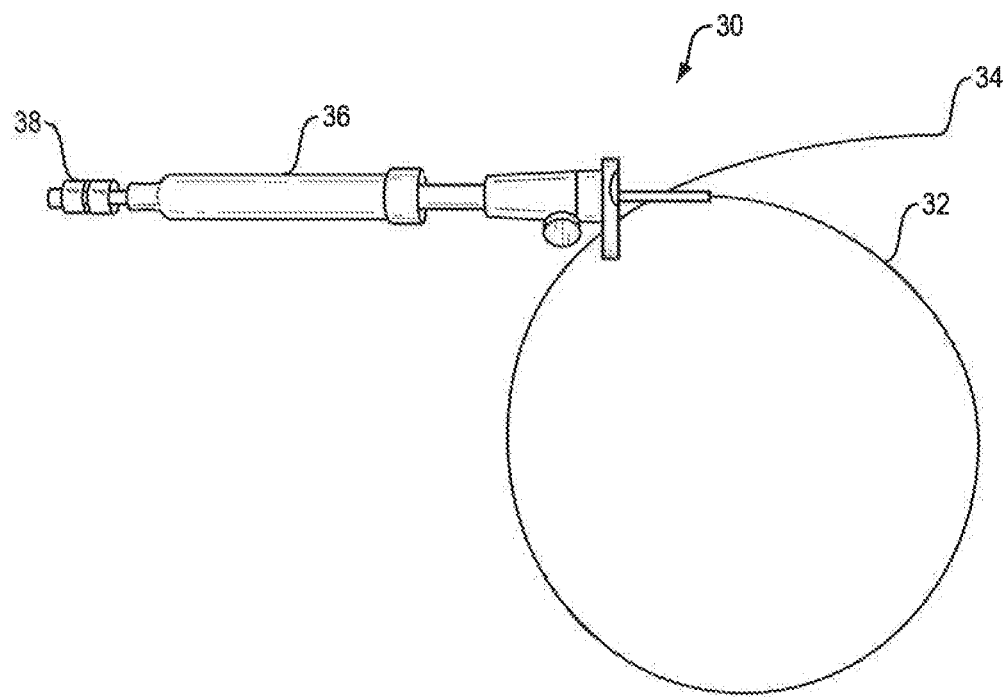
FIG. 2 illustrates a side view of a piercing device according to the teachings herein.

FIG. 2 illustrates aspects of a piercing device 30 that may include the components of the needle piercing system 20. The piercing device 30 may include a handle 36 connected to a sheath 32. A stylet (not shown) may be removably received within the handle 36. The stylet is disposed in the interior of the sheath 32. The handle 36 may house the power source 24 and/or the control device 26. The power source 24 may be connected electrically to the needle actuator 22 located at a distal end of the sheath 32. The power source 24 may be connected electrically, mechanically or both to the control device 26. A stylet handle 38 may connect to a stylet located within a needle 34. The needles 34 may be located at a distal end of the sheath 32.

Figure 3:
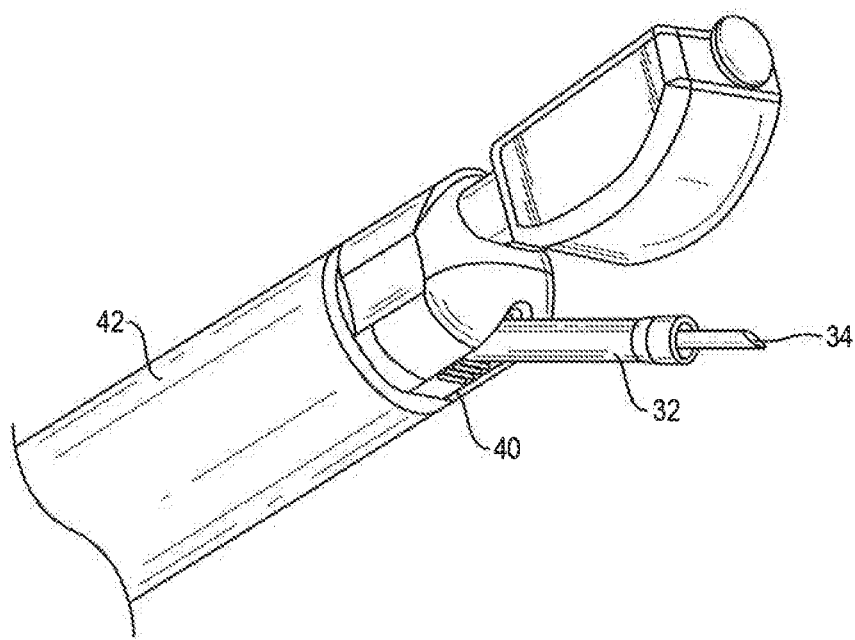
FIG. 3 illustrates a perspective view of a portion of a piercing device included in a catheter of a bronchoscope according to the teachings herein.

FIG. 3 illustrates the sheath 30 that extends from a working channel 40 of a catheter 42 of a bronchoscope, and includes therein the needle 34. The sheath 32 may be received within the catheter of bronchoscope or may be inserted directly into a lumen of a patient if inserted into a bronchoscope or a comparable device, the handle 36 may connect to the bronchoscope after passing the sheath 32 through the bronchoscope handle into the catheter 42. The sheath 32 may include a portion of the needle actuator 22 located at or near the distal end of the sheath 32.

Figures 1, 4:
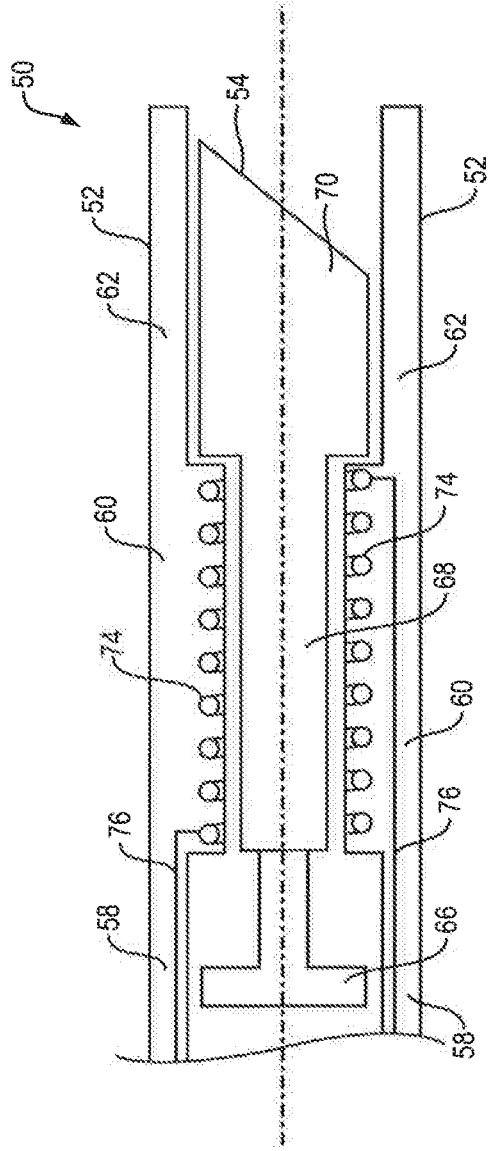
Figures 2, 4:
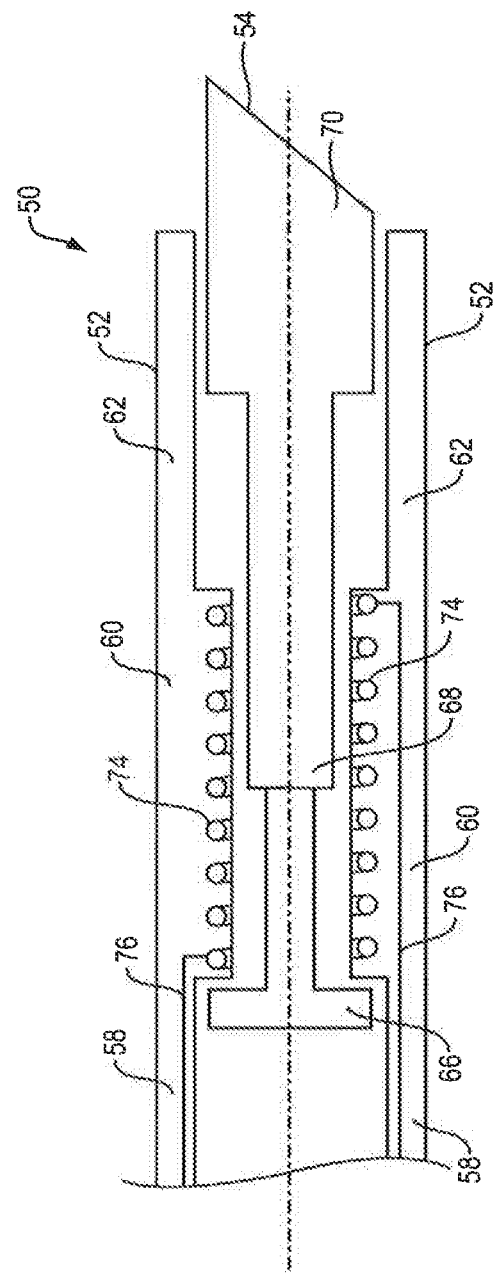

FIGS. 4-1 and 4-2 illustrate a distal end of a piercing device 50 in retracted and extended modes of operation. The piercing device 50 may include a sheath 52 having a lumen for receiving a needle 54. The sheath 52 may include a proximal needle section 58, an actuator section 60 and a distal needle section 62. The proximal needle section 58 and the distal needle section 62 include inner walls having diameter values that are greater than a diameter value of an inner wall of the actuator section 60.

The actuator section 60 may include a conductive coil 74 embedded within the sheath 52 (as shown), a coil lodged against the inner wall of the actuator section 60, or a combination thereof. Leads 76 connect the ends of the coil 74 to the power source 24. The leads 76 may be embedded within the sheath 52 (as shown), may traverse along the inner wall of the sheath 52, or a combination thereof.

The needle 54 may include a proximal section 66, a shaft section 68 and a distal section 70. The proximal section 66 and the distal section 70 may include at least a portion having outer diameter values that are greater than the diameter value of the inner wall of the actuator section 60. The needle 54 may include ferromagnetic material.

Prior to activation of the coil 74 the distal end of the needle 54 may be located proximal or distal to the proximal end of the coil 74. In this configuration, the distal section 70 of the needle 54 would be sized so that it can fit within the actuator section 60. When a DC current is applied to the coil 74, the coil 74 generates a magnetic field causing the ferromagnetic needle 54 or ferromagnetic component(s) of the needle 54 to become magnetized. The magnetized needle 54 accelerates towards the generated magnetic field. As the ferromagnetic needle 54 approaches, inductance increases, completing a positive feedback loop such that the pull on the projectile and magnetic field created by the coil 74 increases. The acceleration reaches a peak when the needle 54 is completely enclosed by the coil 74, where further travel decreases the loop's inductance. At the point when the needle 54 is completely enclosed by the coil 74, current through the coil 74 may be abruptly turned off so a reverse force due to the magnetic field is not applied to the needle 54.

As shown in FIG. 4-2, distal travel of the needle 54 ends either by tissue resistance experienced by the needle 54 or when the proximal section 66 makes contact with the protruding inner wall of the actuator section 60.

After extension of the needle 54, the current in the coil 74 may be reversed. The reversed current cause the coil 74 to generate a proximal magnetic force on the needle 54. The proximal magnetic force causes the needle to return to the sheath 52. The direction of current may be alternated in order to move the needle 54 in and out of the sheath 52. The process of alternating current in the coil 74 can be repeated at various frequencies (e.g., 1-100 Hz) for repeatedly piercing the target tissue.

FIGS. 5A and 5B illustrate a piercing device 80 that is similar to the piercing device 50 of FIG. 4-1 except that a spring device 82 provides a proximal force to a needle 54-1. The proximal section 66-1 includes one or more flanges for receiving a proximal end of the spring device 82. A proximal end of the actuator section 60 receives a distal end of the spring device 82. The spring device 82 may provide the proximal force only after a predefined amount of compression. Other proximal force producing devices may be used.

FIG. 6 illustrates a curve showing force on the needle based on a gap between the coil and the needle. The formula for that curve is as follows:

$$F = \frac{(N \cdot I)\mu_0 A}{(2g^2)}$$

$\mu_0 = 4\pi \times 10^{-7}$
A=cross sectional area of needle
g=gap between needle and coil
I=current
N=number of turns of coil.

The distance the needle extends beyond the sheath for penetration may vary. The distance may be 0.5-1 cm for a 21G needle. A minimum force for getting the needle to penetrate soft tissue is approximately 2 Newtons (N). To attain a 2N force, g=0.5 cm, A=0.32 cm$^2$, N=2000 turns, I=2.5 A. The coil 74 may have a diameter of 0.001 in. The sheath 52 may insulate the coil 74 from the patient.

Figure 7:
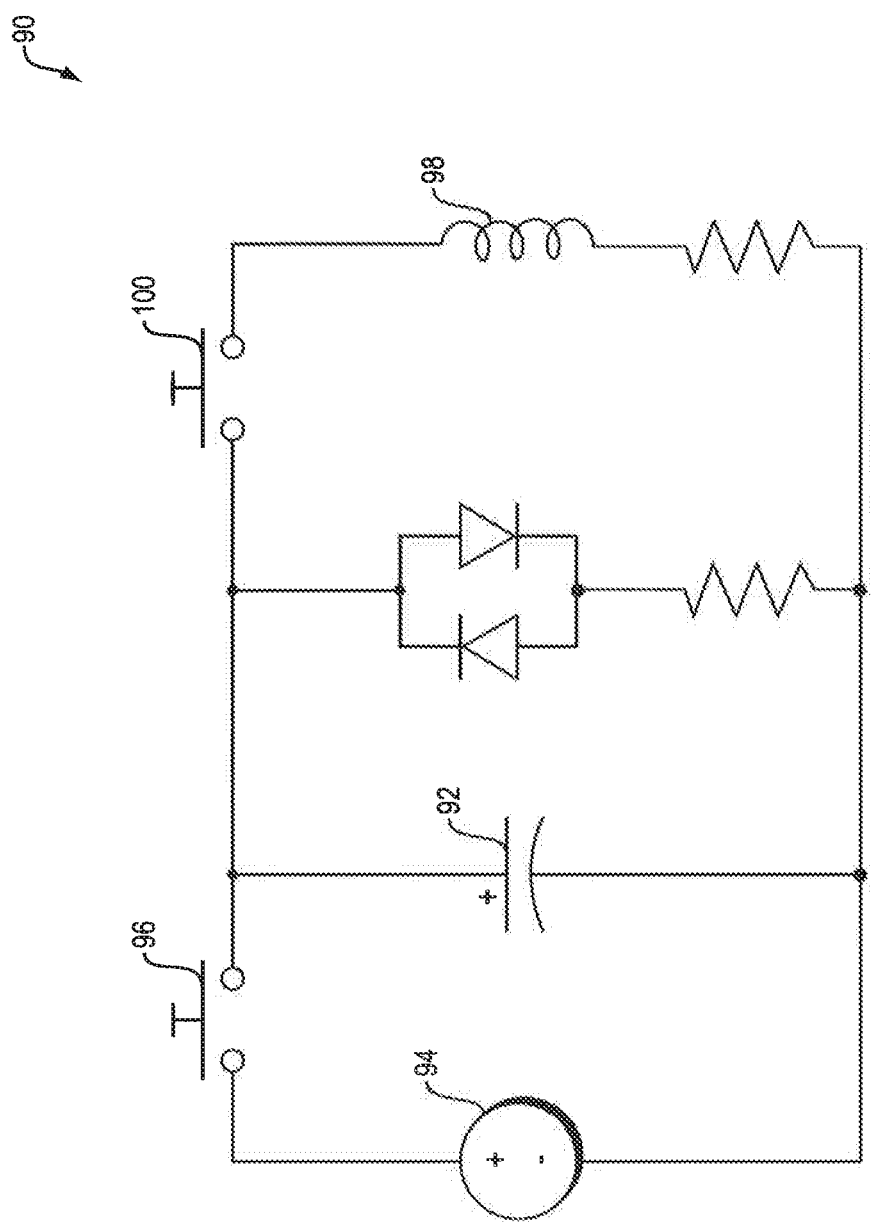
FIG. 7 illustrates a circuit diagram of at least a portion of the electrical components of the piercing system.

FIG. 7 illustrates a circuit 90 that may be used by the needle piercing system 20 of FIG. 1 for applying a single directional force to the needle. The circuit 90 may include one or more capacitors 92 that are charged by a DC power supply 94 based on operation of a charging switch 96. The capacitors 92 discharge to a coil 98 upon activation of a discharge switch 100. Other circuit components such as safety components (e.g., diodes) and polarity switching components may be used.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

The omission in the following claims of any aspect of subject matter that is disclosed herein is not a disclaimer of such subject matter, nor should it be regarded that the inventors did not consider such subject matter to be part of the disclosed inventive subject matter.

LISTING OF REFERENCE NUMERALS

20 needle piercing system
22 needle actuator
24 power source
26 control device
30 piercing device
32 sheath
34 needle
36 handle
38 stylet handle
40 working channel
42 catheter
50 piercing device
52 sheath
54 needle
54-1 needle
58 proximal needle section
60 actuator section
62 distal needle section
66 proximal section
68 shaft section
70 distal section
74 coil
76 leads
80 piercing device
82 spring device
90 circuit
92 capacitors
94 DC power supply
96 charging switch
98 coil
100 discharge switch

The invention claimed is:

1. A device comprising:
a sheath comprising a proximal end and a distal end;
a needle slidably received within the distal end of the sheath; and
an actuator component located at least partially within the distal end of the sheath, the actuator component configured to apply a magnetic force to the needle; and
wherein the actuator component comprises:
a coil located within the distal end of the sheath; and
a current source in electrical communication with the coil;
wherein the current source comprises:
one or more capacitors;
a DC power source;
a first switch configured to cause the DC power source to charge the one or more capacitors upon activation; and
a second switch configured to cause the one or more capacitors to discharge to the coil upon activation.

2. The device of claim 1, wherein the current source further comprises a component configured to send current from the one or more capacitors through the coil in first and second directions.

3. The device of claim 1, wherein the needle comprises a ferromagnetic component.

4. The device of claim 1, further comprising:
a spring configured to apply a proximal force to the needle.

5. The device of claim 1, wherein at least one of the sheath or the needle comprises:
a first device configured to stop distal motion of the needle; and
a second device configured to stop proximal motion of the needle.

6. The device of claim 1, further comprising a stylet received within at least one of the sheath or the needle.

* * * * *